(12) United States Patent
Fischer

(10) Patent No.: US 6,578,423 B2
(45) Date of Patent: Jun. 17, 2003

(54) ACOUSTIC DETECTION OF DECHUCKING AND APPARATUS THEREFOR

(75) Inventor: Andreas Fischer, Castro Valley, CA (US)

(73) Assignee: LAM Research Corporation, Fremont, CA (US)

(*) Notice: Subject to any disclaimer, the term of this patent is extended or adjusted under 35 U.S.C. 154(b) by 0 days.

(21) Appl. No.: 10/150,022

(22) Filed: May 20, 2002

(65) Prior Publication Data

US 2002/0142492 A1 Oct. 3, 2002

Related U.S. Application Data

(62) Division of application No. 09/817,162, filed on Mar. 27, 2001, now Pat. No. 6,403,322.

(51) Int. Cl.[7] .............................................. G01N 29/00
(52) U.S. Cl. ......................................................... 73/630
(58) Field of Search ...................... 73/597, 630; 438/14

(56) References Cited

U.S. PATENT DOCUMENTS

| | | | |
|---|---|---|---|
| 4,340,462 A | 7/1982 | Koch | |
| 4,431,473 A | 2/1984 | Okano et al. | |
| 4,554,611 A | 11/1985 | Lewin | |
| 4,615,755 A | 10/1986 | Tracy et al. | |
| 4,790,258 A | 12/1988 | Drage et al. | |
| 4,842,683 A | 6/1989 | Cheng et al. | |
| 4,948,458 A | 8/1990 | Ogle | |
| 5,117,121 A | 5/1992 | Watanabe et al. | |
| 5,200,232 A | 4/1993 | Tappan et al. | |
| 5,215,619 A | 6/1993 | Cheng et al. | |
| 5,436,790 A | 7/1995 | Blake et al. | |
| 5,491,603 A | 2/1996 | Birang et al. | |
| 5,788,814 A | 8/1998 | Sun et al. | |
| 5,790,365 A | 8/1998 | Shel | |
| 5,818,682 A | 10/1998 | Loo | |
| 5,858,099 A | 1/1999 | Sun et al. | |
| 5,872,694 A | 2/1999 | Hoinkis et al. | |
| 5,900,062 A | 5/1999 | Loewenhardt et al. | |
| 5,948,986 A * | 9/1999 | Brown | 73/630 |
| 5,956,837 A | 9/1999 | Shiota et al. | |
| 5,996,415 A | 12/1999 | Stanke et al. | |
| 6,004,752 A | 12/1999 | Loewy et al. | |
| 6,022,807 A | 2/2000 | Lindsey, Jr. et al. | |
| 6,057,244 A | 5/2000 | Hausmann et al. | |
| 6,075,375 A | 6/2000 | Burkhart et al. | |
| 6,092,419 A | 7/2000 | Dixon et al. | |
| 6,112,595 A | 9/2000 | Stanke et al. | |
| 6,182,510 B1 * | 2/2001 | Stanke et al. | 73/597 |
| 6,326,149 B1 | 12/2001 | Loewy et al. | |

FOREIGN PATENT DOCUMENTS

| | | |
|---|---|---|
| EP | 0 822 590 | 2/1998 |
| JP | 09214257 | 2/1999 |
| JP | 10032604 | 8/1999 |

\* cited by examiner

*Primary Examiner*—John F. Niebling
*Assistant Examiner*—Andre C Stevenson
(74) *Attorney, Agent, or Firm*—Burns, Doane, Swecker & Mathis, LLP

(57) ABSTRACT

In a vacuum processing chamber, a monitoring arrangement for detecting when a substrate is sufficiently dechucked by an electrostatic clamp to allow safe movement thereof by a transfer mechanism such as a pin lifter. The monitoring arrangement includes an acoustic generator which outputs a sound wave at the resonant frequency of the substrate and the dechucking condition is detected when the sound wave is adsorbed by the substrate. The arrangement can be used during processing of wafers such as plasma etching or chemical vapor deposition.

11 Claims, 1 Drawing Sheet

ACOUSTIC DETECTION OF DECHUCKING AND APPARATUS THEREFOR

This application is a divisional of application Ser. No. 09/817,162, filed on Mar. 27, 2001 now U.S. Pat No. 6,403,322.

FIELD OF THE INVENTION

The present invention relates to a method of detecting completion of dechucking of a substrate and apparatus therefor. The method is useful for detecting dechucking of a semiconductor wafer during processing such as plasma processing in a vacuum chamber. The apparatus for detecting the completion of dechucking can be incorporated in a lift pin arrangement for lifting substrates such as semiconductor wafers or flat panel display substrates.

BACKGROUND OF THE INVENTION

Various types of equipment exist for semiconductor processing such as plasma etching, ion implantation, sputtering, rapid thermal processing (RTP), photolithography, chemical vapor deposition (CVD) and flat panel display fabrication processes wherein etching, resist stripping, passivation, deposition, and the like, are carried out. In such systems, it is necessary to transport and/or support the substrate by lift pin mechanisms. Such lift pin mechanisms can be used for temporarily supporting the substrates during transfer, thermal, chemical, optical and other treatments of the substrates.

Plasma generation is used in a variety of such semiconductor fabrication processes. Plasma generating equipment includes parallel plate reactors such as the type disclosed in commonly owned U.S. Pat. No. 4,340,462, electron cyclotron resonance (ECR) systems such as the type disclosed in commonly owned U.S. Pat. No. 5,200,232 and inductively coupled plasma systems such as the type disclosed in commonly owned U.S. Pat. No. 4,948,458. In such plasma processing systems, it is conventional to support the substrate to be treated on a substrate holder within a portion of a plasma process chamber. Further, it is conventional to hold the substrate on the substrate holder by mechanical and/or electrostatic clamping mechanisms. An example of a mechanical clamping system is disclosed in U.S. Pat. No. 4,615,755 and an example of an electrostatic chucking (ESC) arrangement is disclosed in U.S. Pat. No. 4,554,611.

In order to transfer a substrate such as a wafer into a substrate processing chamber, it is conventional to utilize robot arm and lift pin arrangements such as the types disclosed in U.S. Pat. Nos. 4,431,473, 4,790,258, 4,842,683 and 5,215,619. In order to lower the wafer onto a substrate holder, it is conventional to use a lift pin arrangement such as the type disclosed in U.S. Pat. No. 4,431,473 wherein four lift pins are arranged in a circular pattern which is concentric with a substrate in the form of a wafer.

U.S. Pat. No. 5,948,986 discloses a technique utilizing acoustic waves for monitoring the presence of a substrate prior to electrostatically clamping the substrate on an ESC. U.S. Pat. No. 6,182,510 B1 discloses an apparatus utilizing acoustic waves to measure wafer temperature during processing thereof, e.g., the acoustic waves are transmitted to the wafer using lift pins as pin transducers. U.S. Pat. No. 5,872,694 discloses an apparatus for determining warpage in a wafer and providing an optimum clamping voltage with an ESC. Once processing of a wafer is completed, various techniques have been proposed for dechucking a wafer and/or determining when clamping forces have been sufficiently released to allow safe movement of the wafer. See, for example, U.S. Pat. Nos. 5,117,121; 5,491,603; 5,790,365; 5,818,682; 5,900,062; 5,956,837; and 6,057,244.

While techniques have been proposed for monitoring/predicting when wafer dechucking has been completed, such techniques may not adequately determine when the clamping forces on the substrate are reduced sufficiently to allow movement of the substrate from the chuck surface by lifting pins or other transfer mechanism. As such, there is a need in the art for more accurate techniques in determining when a substrate has been sufficiently dechucked to allow transfer thereof from the clamping surface.

SUMMARY OF THE INVENTION

The invention provides a method and apparatus for detecting dechucking of an electrostatic chuck. The apparatus includes a substrate support including an electrostatic chuck adapted to electrostatically clamp a semiconductor substrate on a support surface thereof, an acoustic signal generator adapted to transmit acoustic signals to the semiconductor substrate, and a detection device adapted to detect first and second conditions of the semiconductor substrate, the first condition being detected when the semiconductor substrate is electrostatically clamped and the second condition being detected by the detection device when all of the semiconductor substrate is not electrostatically clamped. In a preferred embodiment, the substrate support includes lift pins which contact the substrate support and the acoustic signal generator transmits the acoustic signals through at least one of the lift pins in contact with the semiconductor substrate. The substrate support can be located in a vacuum chamber such as a plasma etch chamber or CVD chamber for depositing a layer of material on the substrate.

BRIEF DESCRIPTION OF THE DRAWINGS

The foregoing and other objects, features and advantages of the present invention will be more readily understood upon reading the following detailed description in conjunction with the drawings in which.

DETAILED DESCRIPTION OF THE PREFERRED EMBODIMENTS

Figure 1:
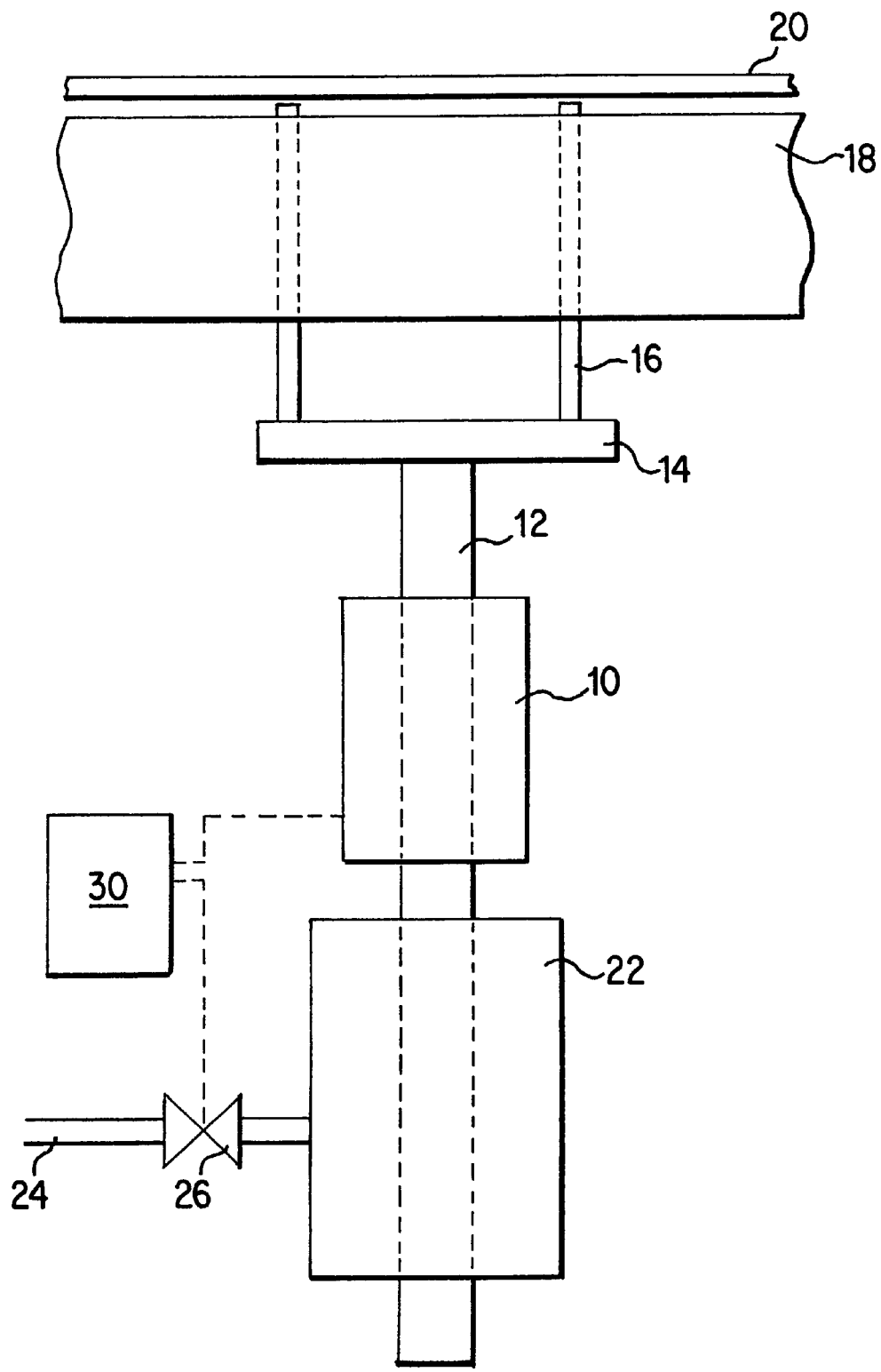
FIG. 1 shows a lift pin arrangement incorporating an acoustic monitoring arrangement in accordance with the invention.

In semiconductor processing, wherein a semiconductor substrate such as a silicon wafer is electrostatically clamped to a substrate support, it is desirable to delay movement of the substrate from the support until the clamping forces have been sufficiently reduced. Movement of the substrate prior to a sufficient reduction in the clamping forces can result in damage to the substrate and/or lift pins used to raise and lower the substrate may cause the substrate to pop off the ESC into an undesirable position in the chamber in which the substrate is being processed. The invention provides a technique by which it can be determined when the substrate is sufficiently dechucked to allow safe movement thereof.

During clamping of a substrate with an ESC, one or more high voltage electrodes embedded in a thin semi-conductive layer close to the back side of the substrate can be used to generate electrostatic clamping forces. For example, sufficient voltage (~1000 volts dc) may be applied to the electrodes which in turn create an electric field which generates charges on the lower surface of the substrate which interact with charges on the high-voltage electrodes. The result is a net attractive force between the substrate and the ESC. When processing such as plasma etching, deposition, or the like is completed, the substrate needs to be transported out of the chamber so that a subsequent substrate can be processed in like manner. In doing so, it is necessary to reduce the clamping force between the substrate and the ESC below a threshold value before the substrate can be lifted by a device such as a lift pins arrangement.

The invention provides an improvement over dechucking techniques which rely on empirical determinations to estimate when sufficient dechucking has occurred. However, differences between substrate types and/or shifts in ESC performance over time can lead to inaccuracies in determining when sufficient dechucking has occurred. The invention overcomes such problems by providing a method wherein feedback from the substrate can be used to more accurately determine when it is safe to move the substrate from the ESC. A preferred method according to the invention uses an acoustic signal to monitor the condition of a substrate and determine when it is safe to move the substrate.

According to a first preferred embodiment, a sound signal is delivered to the substrate and a detector such as a sound detector is used to monitor the sound signal reflected from the substrate. Because the reflected sound signal will behave differently when the substrate is clamped to a chuck body than when the clamping forces between the substrate and the chuck body fall below a certain threshold, it is possible to detect when the clamping forces are reduced to an extent sufficient to safely move the substrate.

One technique for delivering the sound signal to the substrate is to use one or more lift pins of a lift pin arrangement to couple the acoustic signal into the substrate. The frequency of the sound wave can be chosen to match the mechanical resonance frequency of the substrate, because as long as the substrate is not completely dechucked from the ESC, the substrate and ESC will form a coupled system. Due to the much greater mass of the coupled system, its resonance frequency will be significantly lower than that of the substrate itself. Due to this coupling effect, the sound wave delivered by the lift pin or pins will not be absorbed by the substrate and instead will be reflected. On the other hand, when the substrate is sufficiently decoupled from the ESC, the delivered sound wave will be at resonance with the mechanical "eigen-frequency" of the substrate and will be absorbed by the substrate.

A sound detection device in the base of the lift pins can be used to monitor the amplitude of the sound wave. When absorption occurs, the amplitude will be significantly higher due to resonant amplification. Thus, when the increase in amplitude is sensed, a "lift" signal can be sent from a controller to the pin lift mechanism to cause the lift pins to raise the substrate off of the ESC. A robot arm of a transport mechanism can then be used to remove the substrate from the chamber.

FIG. 1 shows an arrangement incorporating an acoustic monitoring arrangement in accordance with the invention. The arrangement includes an acoustic transmitter/receiver 10 attached to a shaft 12 of a lift pin pedestal 14. The lift pin pedestal 14 includes lift pins 16 which extend into openings in a chuck body 18. The chuck body includes an ESC in an upper portion thereof for electrostatically clamping a substrate 20 to the upper surface of the chuck body 18. A pneumatically actuated cylinder 22 is effective to raise and lower the substrate 20 by vertically moving the shaft 12. Pressurized gas is supplied through line 24 to the cylinder 22 when valve 26 is opened. For example, a controller 30 can be used to monitor the feedback signal from the transmitter/receiver and operate the valve 26 to raise the lift pins 16 when the transmitter/receiver indicates that resonant amplification has increased above a threshold value-corresponding to when the substrate has been sufficiently dechucked to allow safe movement thereof by the pin lift mechanism.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention as defined by the following claims.

What is claimed is:

1. A method of detecting dechucking of an electrostatic chuck, comprising:

supporting a semiconductor substrate on a substrate support including an electrostatic chuck adapted to electrostatically clamp the semiconductor substrate on a support surface thereof;

generating acoustic signals with an acoustic signal generator adapted to transmit acoustic signals to the semiconductor substrate;

detecting first and second conditions of the semiconductor substrate, the first condition being detected when the semiconductor substrate is electrostatically clamped and the second condition being detected when the semiconductor substrate is in contact with the support surface and is not electrostatically clamped above a threshold clamping force.

2. The method of claim 1, wherein the substrate support includes lift pins which contact the substrate support, the acoustic signal generator transmitting the acoustic signals through at least one of the lift pins in contact with the semiconductor substrate.

3. A method of detecting dechucking of an electrostatic chuck, comprising:

supporting a semiconductor substrate on a substrate support including an electrostatic chuck adapted to electrostatically clamp the semiconductor substrate on a support surface thereof;

generating acoustic signals with an acoustic signal generator adapted to transmit acoustic signals to the semiconductor substrate;

detecting first and second conditions of the semiconductor substrate, the first condition being detected when the semiconductor substrate is electrostatically clamped and the second condition being detected when the semiconductor substrate is not electrostatically clamped above a threshold clamping force;

wherein the acoustic signal generator outputs a sound wave at a mechanical resonance frequency of the semiconductor substrate, the second condition being detected when the detection device detects an increase in absorption of the sound wave by the substrate.

4. A method of detecting dechucking of an electrostatic chuck, comprising:

supporting a semiconductor substrate on a substrate support including an electrostatic chuck adapted to electrostatically clamp the semiconductor substrate on a support surface thereof;

generating acoustic signals with an acoustic signal generator adapted to transmit acoustic signals to the semiconductor substrate;

detecting first and second conditions of the semiconductor substrate, the first condition being detected when the semiconductor substrate is electrostatically clamped and the second condition being detected when the semiconductor substrate is not electrostatically clamped above a threshold clamping force;

wherein the substrate support includes a pin lift mechanism and a controller receives output signals from the detection device indicative of the second condition and actuates the lift pin mechanism to raise the substrate when the second condition is detected.

5. The method of claim 4, wherein the lift pin mechanism is pneumatically operated, the controller actuating the lift pin mechanism by opening a valve supplying pressurized gas to a pneumatic cylinder which raises a shaft attached to a lift pin pedestal.

6. The method of claim 1, wherein the substrate support is located in a plasma etch chamber and the second condition is detected after etching a layer on the semiconductor substrate.

7. The method of claim 1, wherein the substrate support is located in a CVD chamber and the second condition is detected after depositing a layer on the semiconductor substrate.

8. The method of claim 1, wherein the substrate support includes openings in the support surface, a heat transfer gas being supplied through the openings to a space between the substrate and the support surface.

9. The method of claim 1, wherein the semiconductor substrate is a silicon wafer and the second condition is detected when a sound wave generated by the acoustic signal generator is absorbed by the wafer.

10. The method of claim 1, wherein the second condition is detected when a sound wave generated by the acoustic signal generator is absorbed by the semiconductor substrate.

11. A method of detecting dechucking of an electrostatic chuck, comprising:

supporting a silicon wafer on a substrate support including an electrostatic chuck adapted to electrostatically clamp the wafer on a support surface thereof;

generating acoustic signals with an acoustic signal generator adapted to transmit acoustic signals to the wafer; and detecting first and second conditions of the wafer, the first condition being detected when the wafer is electrostatically clamped and the second condition being detected when a sound wave generated by the acoustic signal generator is absorbed by the wafer indicating that the wafer is not electrostatically clamped above a threshold clamping force.

* * * * *